United States Patent [19]
Azechi et al.

[11] Patent Number: 5,124,466
[45] Date of Patent: Jun. 23, 1992

[54] CATIONIC SILICONE SURFACTANT AND METHOD OF ITS MANUFACTURE

[75] Inventors: Syuuichi Azechi; Noriyuki Meguriya; Masaki Tanaka, all of Gunma, Japan

[73] Assignee: Shin-Etsu Chemical Company Limited, Tokyo, Japan

[21] Appl. No.: 447,933

[22] Filed: Dec. 8, 1989

[30] Foreign Application Priority Data

Dec. 9, 1988 [JP] Japan .................. 63-311727

[51] Int. Cl.$^5$ .................. C07F 7/10; B01F 17/18
[52] U.S. Cl. .................. 556/425; 252/351; 252/357
[58] Field of Search .................. 252/351, 357; 556/425, 556/413

[56] References Cited

U.S. PATENT DOCUMENTS

| | | | |
|---|---|---|---|
| 4,005,028 | 1/1977 | Heckert et al. | 252/174.15 X |
| 4,006,176 | 2/1977 | Heckert et al. | 252/174.15 X |
| 4,536,298 | 8/1985 | Kamei et al. | 252/3 X |
| 4,981,988 | 1/1991 | Ichinohe et al. | 556/425 |
| 4,986,922 | 1/1991 | Snow et al. | 252/357 X |
| 5,021,532 | 6/1991 | Sugita et al. | 556/425 X |
| 5,068,380 | 11/1991 | Meguriya et al. | 556/413 X |

*Primary Examiner*—Robert L. Stoll
*Assistant Examiner*—Daniel S. Metzmaier
*Attorney, Agent, or Firm*—Millen, White & Zelano

[57] ABSTRACT

A cationic silicone surfactant with excellent surface tension lowering properties and manufacturing method thereof were disclosed. Since a siloxane with a reactive group at one end is used as starting material for production process, the surfactant of the present invention is an AB type block copolymer which has an ideal structure as a surfactant and can exhibit excellent surface tension lowering properties in aqueous systems or solvent systems.

6 Claims, No Drawings

CATIONIC SILICONE SURFACTANT AND METHOD OF ITS MANUFACTURE

FIELD OF THE INVENTION

This invention relates to an cationic silicone surfactant and a manufacturing method thereof.

BACKGROUND OF THE INVENTION

Silicone surfactants have already been reported in the literature, for example the non-ionic organopolysiloxane surfactants described by Maki and Komori in the journal "Kagaku Kogyo", Vol. 73, No. 6, or in the journal "Hyomen", Vol. 7, No. 11, and they are known to be much more effective in lowering surface tension than hydrocarbon surfactants.

As these substances are non-ionic, however, they are of the polyether type. Their dimethylpolysiloxane chain is therefore comparatively short, and their range of application is consequently limited.

Cationic and anionic organopolysiloxane surfactants are also known (Japanese Patent Kokoku No. 49-11760; the term "Japanese Patent Kokoku" as used herein means an "Examined Japanese Patent Publication"). These substances, however, were mixtures of polymers with functional groups at both ends and polymers with functional groups on side chains, or mixtures wherein polymers with functional groups at only one end had been added to the former mixtures, and as a result, these substances did not exhibit good surfactant properties.

In order to widen the range of application of silicone surfactants, therefore, it is necessary to further develop ionic silicone surfactants.

The inventors of this invention carried out intensive research with a view to providing a solution to this problem. Then, using a siloxane which was reactive at one end as starting material to synthesize a surfactant, it was found that a cationic silicone surfactant with extremely good surface tension lowering properties could be obtained, and this led to the present invention.

SUMMARY OF THE INVENTION

The first object of this invention, therefore, is to provide a cationic silicone surfactant with excellent surface tension lowering properties.

A second object of this invention is to provide a method of manufacturing a cationic silicone surfactant with excellent surface tension lowering properties.

The above objects of the present invention are attained by a cationic silicone surfactant represented by the general formula (I), and by the method of manufacturing it herein described.

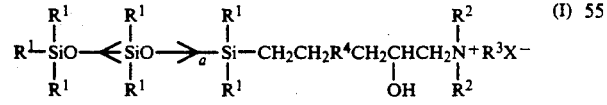

The cationic surfactant of this invention has an effect which is due to the low surface tension of siloxane itself. In addition, it is an AB type block copolymer which has an ideal structure as a surfactant, therefore, it exhibits excellent capacity as a surfactant. Moreover, it is not only easy but also quite quantitative to manufacture it.

Moreover, as the silicone surfactant of this invention is cationic, it can fulfil novel purposes for which conventional silicone surfactants are of no use.

DETAILED DESCRIPTION OF THE INVENTION

In the foregoing formula (I), each $R^1$ represents an unsubstituted or halogen-substituted monovalent hydrocarbon residue of 1 to 20 carbon atoms, where $R^1$ can be indentical to or different from one another. Suitable examples of a monovalent hydrocarbon residue represented by $R^1$ include alkyl groups such as methyl, ethyl, propyl, butyl, pentyl, hexyl, octyl dodecyl, etc., aryl groups such as phenyl, tolyl, benzyl, and naphthyl, etc., and substituted hydrocarbon residues formed by replacing the hydrogen (s) of the above-cited monovalent hydrocarbon residues by hydroxyl group(s) or halogen(s) such as fluorine, chlorine, bromine, etc. In particular, it is desirable that at least 80% of the group $R^1$ is methyl.

$R^2$ presents a hydrogen atom, or an unsubstituted or hydroxyl-substituted monovalent hydrocarbon residue of 1 to 10 carbon atoms. Suitable examples include alkyl groups such as methyl, ethyl, propyl, butyl, pentyl, hexyl, octyl, etc., aryl groups such as phenyl, benzyl, tolyl, etc., and substituted hydrocarbon residues formed by replacing the hydrogen(s) of the above-cited hydrocarbon residues by hydroxyl group(s). In particular, methyl is preferred as $R^2$.

$R^3$ represents a hydrogen atom, or an unsubstituted or hydroxyl-substituted monovalent hydrocarbon residue of 1 to 20 carbon atoms. Specific examples include alkyl groups such as methyl, ethyl, propyl, butyl, pentyl, hexyl, octyl, dodecyl, etc., aryl groups such as phenyl, tolylbenzyl, naphthyl, etc., and the substituted hydrocarbon residues formed by replacing the hydrogen(s) of the above-cited hydrocarbon residues by hydroxyl group(s). In particular, methyl is preferred as $R^3$.

$R^4$ represents an unsubstituted or halogen- or hydroxyl-substituted divalent hydrocarbon residue of 1 to 10 carbon atoms, or a group formed by replacing less then one-half of the carbon atoms contained in said hydrocarbon residue by oxygen. In particular, the group $-CH_2O-$ is preferred as $R^4$.

X represents a halogen selected from fluorine, chlorine, bromine and iodine; however, chlorine is the best. "a" is a number satisfying the inequality $0 \leq a \leq 20$.

The surfactant of this invention represented by general formula (I) is obtained by reacting an organopolysiloxane with an Si—H bond at one end represented by the formula:

with a compound of general formula:

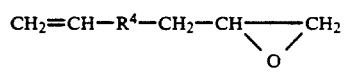

in the presence of a platinum catalyst so as to obtain an organopolysiloxane represented by the formula:

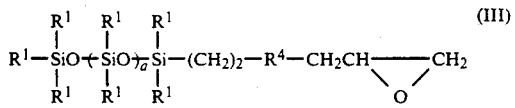
(III)

and then reacting this organopolysiloxane with an amine which is for example represented by general formula:

$$R^2{}_2NH \quad (IV)$$

under heating and further reacting with alkylhalide represented by general formula:

$$R^3X \quad (V)$$

In this case, said compound of general formula (II) may be obtained by reacting a hexaorganocyclotrisiloxane with a triorganosilanol in the presence of, for example, a penta-coordinated silicon compound catalyst represented by the formula:

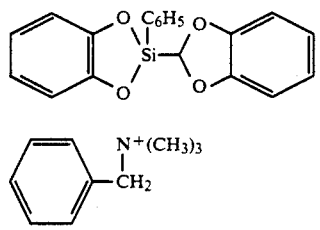

to give an organopolysiloxane terminated by a silanol group at one end represented by the formula:

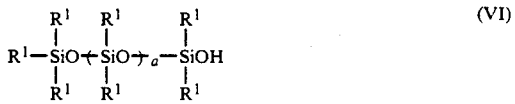
(VI)

and then removing hydrochloric acid from a reaction mixture of the resulting polymer and a diorganochlorosilane of the type $[H(R^1)_2SiCl]$ by means of a dehydrochlorinating agent such as trimethylamine.

The organopolysiloxane thus obtained not only retains the effect of the low surface tension of siloxane itself, but also, as a reactive siloxane at one end is used as the starting material, the product is an AB type block copolymer which has an ideal structure as a sufactant. As a result, the organopolysiloxane of this invention exhibits excellent surface tension lowering properties in both aqueous systems and solvent systems. It may therefore be used as a foaming agent, penetrating agent or cleaner, and as the siloxane fragment has an affinity for silicone oil, it also performs very well in the form of a silicone oil emulsion.

EXAMPLES

We shall now describe the invention in more detail with reference to specific examples. It should however be understood that the invention is in no way limited to these examples.

EXAMPLE 1

90 g of trimethylsilanol, 300 g of toluene and 120 g of triethylamine were introduced successively into a three-necked flask of capacity 1 l equipped with a thermometer, stirrer and reflux condenser. 94.5 g of dimethyl-mono-chlorosilane were then dripped in at room temperature with stirring, and stirring was continued for 3 hours. After washing the reaction mixture obtained with water, a siloxane represented by the formula:

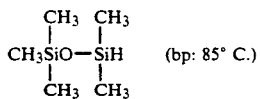

was obtained by distillation.

200 g of the siloxane thus obtained, 300 g of toluene, 169 g of an epoxy compound represented by the formula:

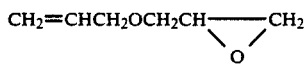

and 0.1 g of a 2% isopropanol solution of platinic acid chloride $(H_2PtCl_6 \cdot 6H_2O)$ were introduced into a three-necked flask of capacity 1 l similar to the above, and the mixture was heated at 70° C.-90° C. for 5 hours. After confirming that the absorption of the Si—H bond (2150 cm$^{-1}$) had disappeared on the IR spectrum of the reaction mixture, the solvent was distilled off from the reaction mixture under reduced pressure so as to obtain a liquid. This liquid was analyzed by gas chromatography, and found to be 97% pure with 280 epoxy equivalents (calculated value 262). It was thus verified that the liqid was an epoxysiloxane represented by the following structural formula:

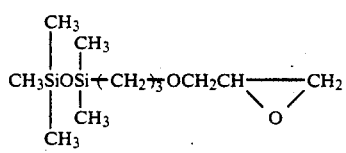

In the same flask as used above, 262 g of the epoxysiloxane obtained above and 300 g of isopropyl alcohol were placed, and stirred at room temperature. To the stirred mixture, 135 g of a 50% water solution of dimethylamine was added dropwise, and the stirring was continued for additional one hour at room temperature. Subsequently, the reaction mixture was stirred at 50°-60° C. for 2 hours, and then the solvent and water were removed therefrom under reduced pressure. Thus, a liquid comprising a compound represented by the following structural formula and having the amine equivalent of 320 (theoretical value: 307) was obtained.

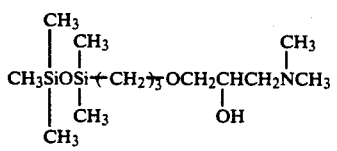

Then, 307 g of the above siloxane and 200 g of butanol were placed in an autoclave equipped with a thermometer and a stirrer, and thereinto was bubbled 100 g of methyl chloride at about 70° C. with stirring under internal pressure of 5-6 Kg/cm$^2$. After the conclusion of the bubbling, the stirring was further continued for 5 hours. The solvent was distilled away under reduced pressure after the change in pH value of the reaction system to neutrality was ascertained with pH test paper. Thus, a solid comprising a compound represented by the following structural formular was obtained.

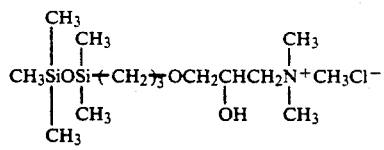

This solid was soluble in water, and 98% thereof was ascertained to be the quaternary ammonium salt by the titration of free chlorine ion (The thus obtained compound will be called Surfactant A, hereinafter.).

An elemental analysis was carried out. The calculated value were: C: 47.0%, H: 10.2%, Cl: 9.9%, N: 3.9%, Si: 15.7%. The experimental values were: C: 46.1%, H: 10.1%, Cl: 9.7%, N: 4.1%, Si: 16.1%. It is seen that the experimental values agree well with the calculated values (% indicates weight percent).

EXAMPLE 2

666 g of hexamethylcyclo-trisiloxane, 90 g of trimethylsilanol and 0.1 g of the penta-coordinated silicon compound catalyst with the structural formula given in this specification were introduced into a three-necked flask of capacity 1 l equipped with a thermometer, stirrer and reflux condenser, and reacted together at 80° C. with stirring for 16 hours to synthesize a siloxane terminated by a silanol group at one end which is represented by the formula:

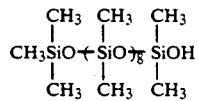

60 g of trimethylamine and 94.5 g of dimethylmonochlorosilane were then dripped into the above obtained reaction mixture at room temperature with stirring, and stirring was continued for 5 hours. After washing the reaction mixture obtained with water, a liquid polysiloxane represented by the formula:

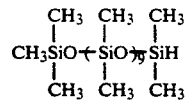

was obtained.

A liquid product represented by the following average formula was obtained in the same manner as in Example 1:

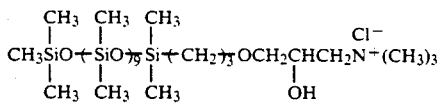

Since a content of the quaternary ammonium salt in this product turned out to be below 80 wt. % by the determination of free chlorine ion, a 200 g portion of the product was shaken with a mixture of 500 g of hexane and 500 g of methanol in a separatory funnel. The methanol layer taken out was subjected to a stripping treatment under reduced pressure to yield 160 g of a solid.

The thus purified solid was insoluble in water, but soluble in ethylene glycol and methanol. The content of the quaternary ammonium salt in the purified solid was evaluated to be 96 wt. % from the determination of free chlorine ion (The purified solid described above will be called Surfactant B, hereinafter.).

An elemental analysis was carried out. The caluated values were: C: 37.5% H: 8.8%, Cl: 3.5, N: 1.4%, Si: 30.1%. The experimental values were: C: 37.9%, H: 8.1%, Cl: 3.2%, N: 1.3%, and Si: 31.2%. It is seen that the experimental values agree well with the calculated values (% indicates weight per cent).

EXAMPLE 3

291.9 g of an amination product of the liquid polysiloxane

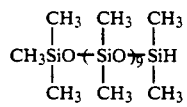

obtained in Example 2, which was represented by the following formula;

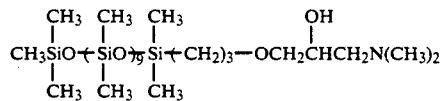

200 g of butanol and 61.6 g of butyl bromide were placed in the same three necked flask as used in Example 1, and stirred for 4 hours at 100°-120° C. Thereafter, the solvent was distilled away by the stripping under reduced pressure, and the residue was purified in the same manner as in Example 2 to yield a solid containing 98 wt. % of the quaternary ammonium salt represented by the following average formula:

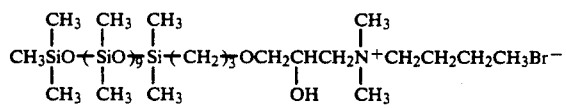

(The purified solid described above will be called Surfactant C, hereinafter.)

The Surfactant C was insoluble in water, but soluble in ethylene glycol and methanol.

An elemental analysis was carried out. The calculated values were: C: 37.8%, H: 8.6%, Br: 7.2%, N: 1.3%, Si: 27.8%. The experimental values were: C: 38.3%, H: 8.5%, Br: 7.1%, N: 1.0% and Si: 29.0%. It is seen that the experimental values agree well with the calculated values (% indicates weight percent).

EXAMPLE 4

The surface tension lowering capacities of Surfactant A, B and C obtained in Examples 1, 2 and 3, were measured with a Counter Balance Vertical Plate (CBVP) surface tension meter. As B and C were not water-soluble, however, ethylene glycol solvent was used. In this measurement, $C_{12}H_{25}N^+(CH_3)_2CH_3Cl^-$ (surfactant D) was used as a comparison sample.

The results are shown in Table 1.

TABLE 1

| Surface Tension Change by various surfactants (dyn/cm) | | | | | |
|---|---|---|---|---|---|
| concentration (mol/l) | $10^{-5}$ | $10^{-4}$ | $10^{-3}$ | $10^{-2}$ | $10^{-1}$ |
| (aqueous system) | | | | | |
| Surfactant A | 41.0 | 21.1 | 20.9 | 20.5 | 20.8 |
| Surfactant D | 71.5 | 69.1 | 58.2 | 39.5 | 38.9 |
| (Ethylene glycol system) | | | | | |
| Surfactant B | 43.1 | 19.9 | 20.5 | 21.0 | 20.3 |
| Surfactant C | 42.9 | 20.1 | 19.7 | 20.8 | 19.8 |
| Surfactant D | 45.5 | 44.7 | 44.8 | 43.9 | 42.1 |

From the results in Table 1, it is proved that the surfactants of this invention have far greater surface tension lowering capacity than conventional hydrocarbon cationic surfactant.

What is claimed is:

1. A cationic silicone surfactant represented by the following general formula (I)

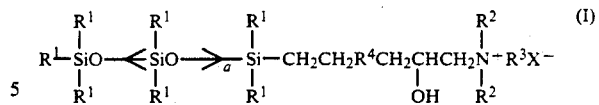

wherein each $R^1$ may be the same as or different from every other $R^1$, and each represents an unsubstituted or halogen-substituted monovalent hydrocarbon residue of 1 to 20 carbon atoms; $R^2$ represents a hydrogen atom, or an unsubstituted or hydroxyl-substituted monovalent hydrocarbon residue of 1 to 10 carbon atoms; $R^3$ represents a hydrogen atom, or an unsubstituted or hydroxyl-substituted monovalent hydrocarbon residue of 1 to 20 carbon atoms; $R^4$ represents an unsubstituted or halogen- or hydroxyl-substituted divalent hydrocarbon residue of 1 to 10 carbon atoms, or a group formed by replacing less than one-half of the carbon atoms contained in said hydrocarbon residue by oxa atom(s); X represents a halogen which is fluorine, chlorine, bromine or iodine; and "a" represents a number satisfying the inequality $3 \leq a \leq 20$.

2. The cationic siloxane surfactant of claim 1, wherein no less than 80% of $R^1$ is methyl.

3. The cationic silicone surfactant of claim 1, wherein $R^4$ is $-CH_2O-$.

4. The cationic silicone surfactant of claim 1, wherein $R^2$ is methyl.

5. The cationic silicone surfactant of claim 1, wherein $R^3$ is methyl.

6. The cationic silicone surfactant of claim 1, wherein X is chlorine.

* * * * *